US00PP14639P29

(12) United States Plant Patent
Schräder

(10) Patent No.: US PP14,639 P2
(45) Date of Patent: Mar. 30, 2004

(54) VERBENA PLANT NAMED 'SUMVERB 06'

(50) Latin Name: *Verbena hybrid*
Varietal Denomination: Sumverb 06

(75) Inventor: Ralf Schräder, Lüdinghausen (DE)

(73) Assignee: Grünewald Veredlings B.V. (NL)

( * ) Notice: Subject to any disclaimer, the term of this patent is extended or adjusted under 35 U.S.C. 154(b) by 0 days.

(21) Appl. No.: 10/378,475

(22) Filed: Mar. 3, 2003

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct early flowering Verbena plant with good lasting quality and reddish-purple colored flowers.

2 Drawing Sheets

Botanical classification: Verbena hybrid.
Varietal denomination: 'Sumverb 06'.

BACKGROUND OF THE INVENTION

The present invention comprises a new and distinct cultivar of Verbena plant known by the varietal name 'Sumverb 06'. The new variety was discovered in August 2001 in a selected breeding program in Lüdinghausen, Germany designed to produce a new variety of Verbena with a hanging habit and great flowering. The new variety was selected from a cross of proprietary unpatented breeding plants Seedling 24 (female parent) and Seedling 48 (male parent). The new variety is a hanging plant as is similar to its parents but has larger flowers than both parents. The new variety has a hanging character similar to 'Temari Violet' (unpatented), but has N78A colored flowers while 'Temari Violet', has N81A colored flowers. The new variety was first asexually reproduced in October 2001 by cuttings in Lüdinghausen, Germany. The new variety has been trial and field tested at Lüdinghausen and has been found to retain its distinctive characteristics and remain true to type through successive propagations.

The following traits distinguish 'Sumverb 06' as a new and distinct cultivar:

1. Flower color.
2. Flower size.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
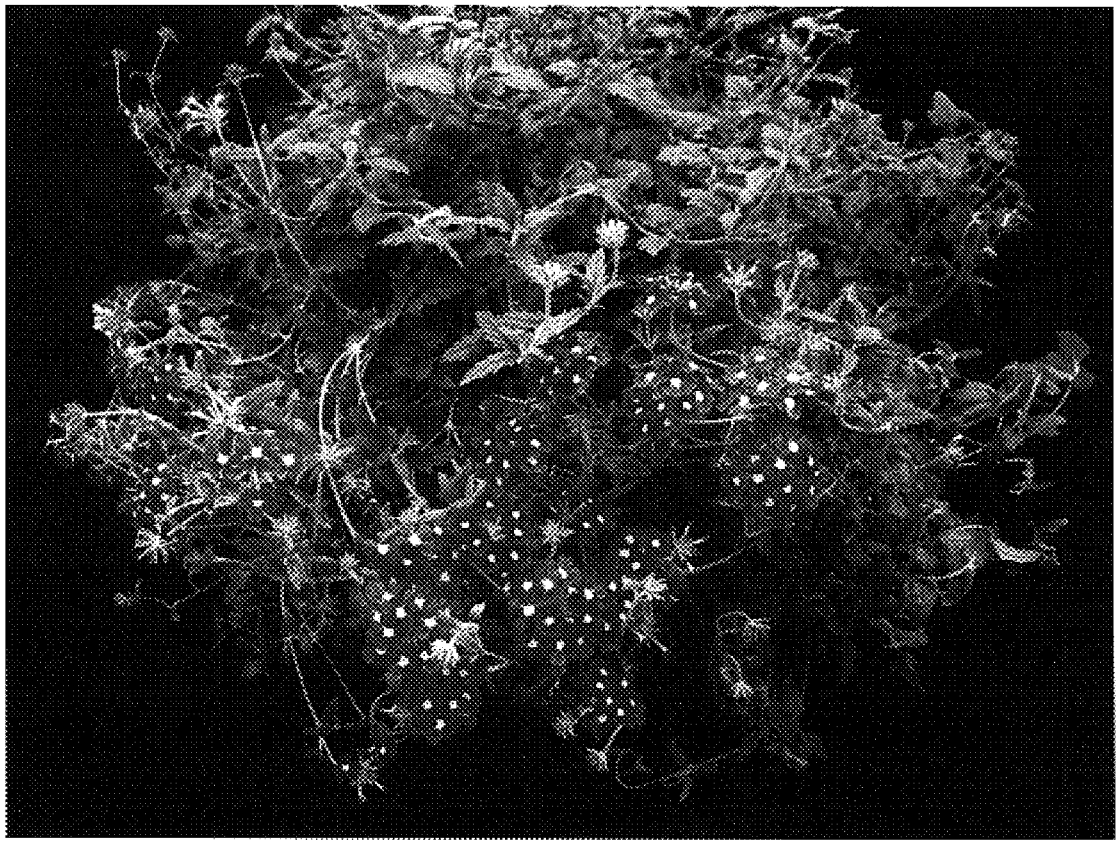
FIG. 1 is a photograph of the plant.
Figure 2:
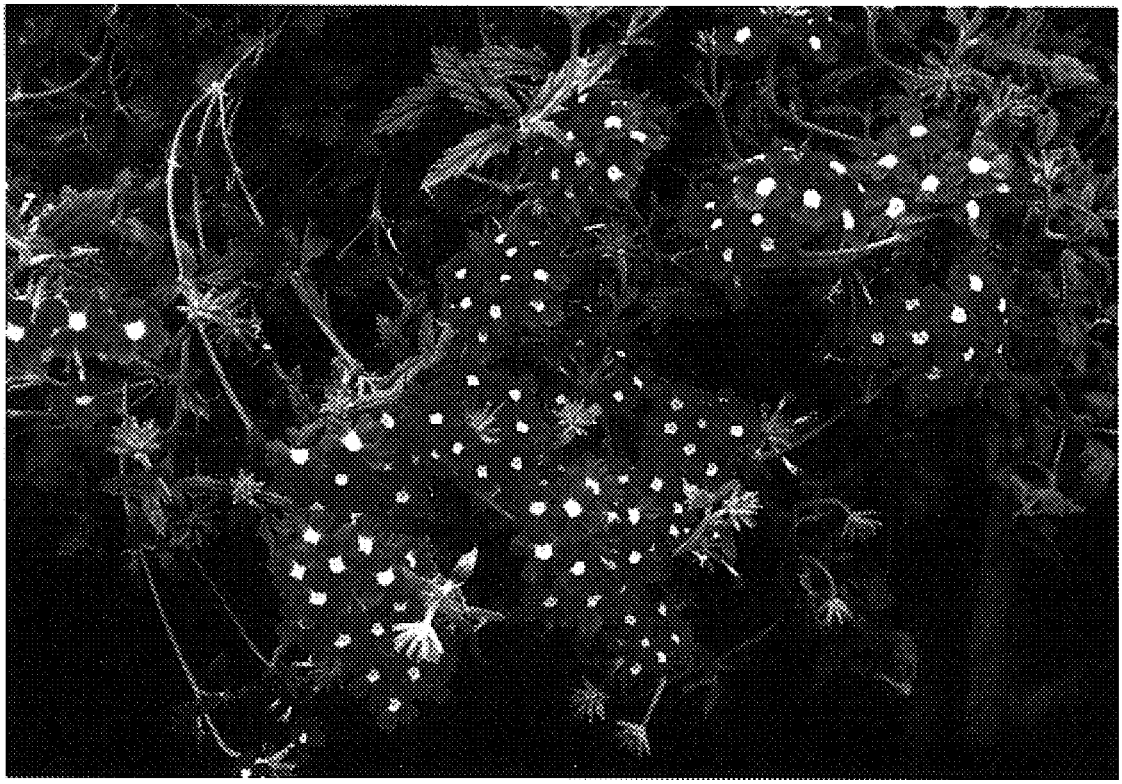
FIG. 2 is a close up view of the blossoms of the new plant.

The following detailed description sets forth characteristics of the new cultivar. The data which defines these characteristics were collected by asexual reproductions by cuttings carried out in Lüdinghausen, Germany. Flowering plants were grown in a greenhouse at 12° C. temperature. The color readings were taken in a greenhouse under natural light. Color references are primarily to The 2001 R.H.S. Colour Chart of The Royal Horticultural Society of London.

PLANT

Form: Mounded.
Height: 25 cm.
Diameter: 30–35 cm.
Vigor: Medium.
Roots:
- *Habit.*—Spreading.
- *Time to initiate roots.*—6 days at 16° C.
- *Time to develop roots.*—10 days at 16° C.

Branching habit: Hanging; good branching.
Lateral branches:
- *Color.*—144B.
- *Texture.*—Pubescent; round.
- *Diameter.*—1.5 mm.
- *Internode length.*—45 mm.

Foliage:
- *Arrangement.*—Single.
- *Size of leaf.*—Length: 34 mm. Width: 30 mm.
- *Shape of leaf.*—Lanceolate.
- *Shape of apex.*—Acute.
- *Shape of base.*—Cordate.
- *Texture.*—Pubescent.
- *Aspect.*—Flat.
- *Margin.*—Crenate.
- *Color.*—Young leaves: Upper surface: 143C. Lower surface: 143A. Mature leaves: Upper surface: 137D. Lower surface: 137A.
- *Petioles.*—Length: 3 mm. Diameter: 1 mm. Color: 139C.
- *Veins.*—Type: Pinnate. Color: Upper surface: 139D. Lower surface: 144C.

FLOWER

Bud (at one day before opening):
- *Natural flowering season.*—Spring to Autumn.
- *Shape.*—Long; 5 parted.
- *Diameter.*—2 mm.
- *Length.*—12 mm.
- *Color.*—N81A in the middle.

Corymb:
*Number of flowers per corymb.*—25.
*Diameter.*—Approximately 55 mm.
*Length.*—Approximately 40 mm.
Corolla:
*Form.*—Zygomorphic.
*Petals/lobes.*—Number: 5. Length: Approximately 12 mm. Width: Approximately 8 mm. Shape: Obovate. Aspect: Flat. Margin: Entire. Texture and appearance: Smooth.
*Color.*—When opening: Upper surface: 72B. Lower surface: 71A. Fully opened: Upper surface: N78D. Lower surface: N78A.
*Throat.*—Color: 1C. Texture: Pubescent.
*Tube color.*—1C.
Calyx:
*Form.*—Fused at base; cylindrical.
*Length.*—17 mm.
*Diameter.*—1 mm.
Sepal:
*Shape.*—Cylindrical; having 5 connected sepals.
*Margin.*—Accuminate.
*Texture.*—Pubescent.
*Color.*—Upper surface: 147B. Lower surface: 147C.
Disease resistance: No resistance to diseases noted to date.
Fragrance: None.
Temperature tolerance: From 0.5° C. to 45° C.

REPRODUCTIVE ORGANS

Stamens:
*Number.*—3.
*Filament length.*—0.5 mm.
*Anthers.*—Shape: Oval. Length: 0.2 mm. Color: 1B.
*Pollen.*—Color: 1B. Amount: Moderate.
Pistil:
*Length.*—12 mm.
*Style.*—Length: 1 mm. Color: 141D.
*Stigma.*—Shape: Oval. Color: 142A.
Seed production: Cuttings only.

I claim:

1. A new and distinct variety of Verbena plant substantially as shown and described.

* * * * *